(12) United States Patent
Hieber et al.

(10) Patent No.: US 9,220,862 B2
(45) Date of Patent: Dec. 29, 2015

(54) PATIENT INTERFACE SYSTEM WITH ARTICULATING FOREHEAD PAD ATTACHMENT

(71) Applicant: KONINKLIJKE PHILIPS N.V., Eindhoven (NL)

(72) Inventors: Robert Earl Hieber, Export, PA (US); Kevin Shick, Claridge, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/406,600

(22) PCT Filed: Jun. 7, 2013

(86) PCT No.: PCT/IB2013/054682
§ 371 (c)(1),
(2) Date: Dec. 9, 2014

(87) PCT Pub. No.: WO2013/190421
PCT Pub. Date: Dec. 27, 2013

(65) Prior Publication Data
US 2015/0151064 A1    Jun. 4, 2015

Related U.S. Application Data

(60) Provisional application No. 61/661,989, filed on Jun. 20, 2012.

(51) Int. Cl.
*A61M 16/06* (2006.01)
*A61M 16/08* (2006.01)

(52) U.S. Cl.
CPC .......... *A61M 16/065* (2014.02); *A61M 16/0622* (2014.02); *A61M 16/0638* (2014.02); *A61M16/0655* (2014.02); *A61M 16/0683* (2013.01); *A61M 16/0825* (2014.02); *A61M 2205/586* (2013.01)

(58) Field of Classification Search
CPC . A61M 15/08; A61M 16/00; A61M 16/0057; A61M 16/06; A61M 16/0605; A61M 16/0611; A61M 16/0616; A61M 16/0622; A61M 16/0633; A61M 16/0638; A61M 16/0644; A61M 16/0655; A61M 16/0666; A61M 16/0683; A61M 16/08; A61M 16/0816; A61M 16/0825; A61M 16/085; A61M 16/0858; A61M 16/0875; A61M 16/10; A61M 16/1065; A61M 16/20; A62B 18/00; A62B 18/003; A62B 18/02; A62B 18/08; A62B 18/084
USPC ............. 128/200.22, 201.12, 201.13, 201.14, 128/201.22, 204.18, 205.25, 205.27, 128/206.11, 206.12, 206.21, 206.24, 128/206.26, 206.27, 207.11, 207.12, 128/207.13, 207.17, 207.18, 912
See application file for complete search history.

(56) References Cited

U.S. PATENT DOCUMENTS

2011/0023883 A1    2/2011    Hieber

FOREIGN PATENT DOCUMENTS

| WO | WO2011107899 A1 | 9/2011 |
| WO | WO2012020359 A1 | 2/2012 |

*Primary Examiner* — Annette Dixon
(74) *Attorney, Agent, or Firm* — Michael W. Haas

(57) ABSTRACT

A patient interface device (8, 108) includes a mask component (16, 116) structured to engage a face of the patient, a head support member (22, 122) structured to rest on a head of the patient, and a coupling arm (24, 124) having a first end (40, 134) coupled to the mask component and a second end (42, 136) coupled to the head support member. The second end of the coupling arm is coupled to the head support member in a manner wherein the mask component is selectively moveable relative to the head support member in multiple planes such that the mask component can be rotated at least 180 degrees in a plane that is parallel to the patient's face.

16 Claims, 28 Drawing Sheets

PATIENT INTERFACE SYSTEM WITH ARTICULATING FOREHEAD PAD ATTACHMENT

CROSS-REFERENCE TO RELATED APPLICATIONS

This patent application claims the priority benefit under 35 U.S.C §371 of international patent application no. PCT/IB2013/054682, filed Jun. 7, 2013, which claims the priority benefit under 35 U.S.C. §119(e) of U.S. Provisional Application No. 61/661,989 filed on Jun. 20, 2012, the contents of which are herein incorporated by reference.

BACKGROUND OF THE INVENTION

1. Field of the Invention

The present invention pertains to patient interface systems, and, in particular, to a patient interface device structured to deliver a flow of breathing gas to a patient that includes a mechanism for providing multi-axis access to the patient's face as needed.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Non-invasive ventilation interface devices are typically worn by patients for several days. This extended period of treatment necessitates periodic, temporary access to the mouth and nose by the caregiver for things such as eating, drinking, speaking, and/or medication. One option for gaining such access is to remove the interface device. While effective, this solution causes all sizing settings to be completely lost in the process, necessitate a re-sizing when the interface device is to be put back into place on the patient. Another option is provided by the interface device described in United States Patent Application Publication No. 2011/0023883 ("the '883 application:"), which maintains sizing by providing a hinge between the mask and headgear for oro-nasal access. In particular, the interface device described in the '883 application includes a mask system that allows the mask to lift up-and-away from the wearer's face without the need to remove the headgear. However, the mask can only be lifted away from the face on a single-axis hinge in a single plane that is perpendicular to the wearer's face. This is a problem as the mask's orientation remains fixed in all but the plane of movement. Therefore, the elbow connector and attached circuit (i.e., delivery conduit) takes-up space and limits the range of motion and ability to "lock" the mask into place. Furthermore, the weight of the mask creates notable torque on the hinge, further complicating any workable "locking" solution. Thus, in that system, the mask must be manually held in the up-and-away position.

SUMMARY OF THE INVENTION

Accordingly, it is an object of the present invention to provide a patient interface device that overcomes the shortcomings of conventional patient interface devices. This object is achieved according to one embodiment of the present invention by providing patient interface device that includes a mechanism for providing multi-axis access to the patient's face as needed.

It is yet another object of the present invention to provide a method of adjusting a patient interface that does not suffer from the disadvantages associated with conventional adjustment techniques. This object is achieved by providing a method that wherein the patient interface device may be moved in multiple axes.

In one embodiment, a patient interface device is provided that includes a mask component structured to engage a face of the patient, a head support member structured to rest on a head of the patient, and a coupling arm having a first end coupled to the mask component and a second end coupled to the head support member. The second end of the coupling arm is coupled to the head support member in a manner wherein the mask component is selectively moveable relative to the head support member in multiple planes such that the mask component can be rotated at least 180 degrees in a plane that is parallel to a top surface of the head support member.

In another embodiment, a method of adjusting a patient interface device including a mask component, a head support member having a bottom surface structured to rest on a head of the patient and a top surface opposite the bottom surface, and a coupling arm having a first end coupled to the mask component and a second end coupled to the head support member is provided. The method includes moving the mask component from a first condition wherein the mask component is located in a first position and engages a face of the patient to a second condition wherein the mask component is located in a second position that is 180 degrees from the first position relative to a plane that is parallel to the top surface of the head support member, wherein the mask component has front side and a rear side opposite the front side, the rear side of the mask component being structured to engage the face of the patient, and wherein in the second condition the rear side of the mask component faces toward the top side of the head support member and the front side of the mask component faces away from the top side of the head support member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
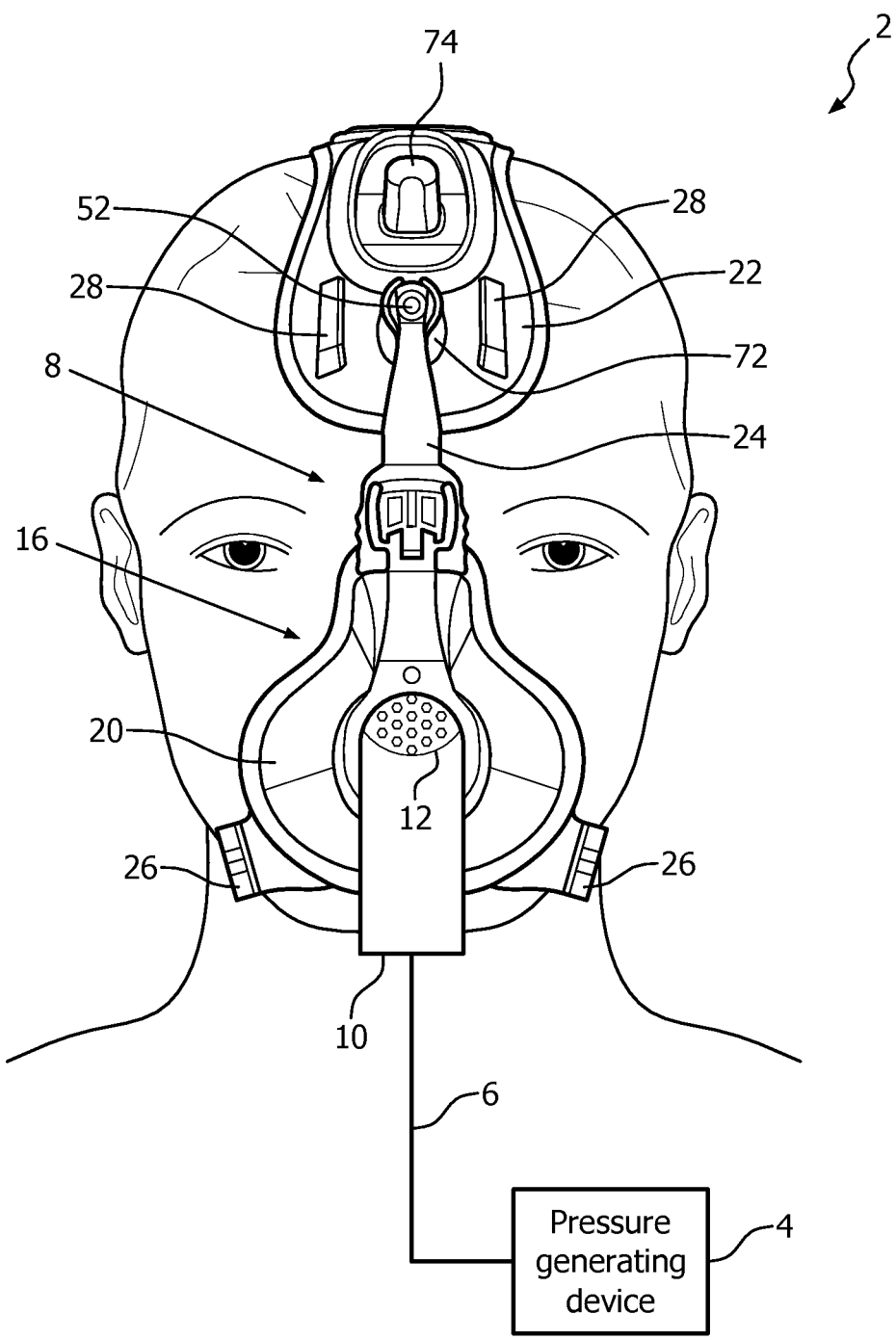
FIGS. 1-4 are schematic diagrams of a system adapted to provide a regimen of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment is generally shown in FIGS. 1 (front view) and 2 (side view). System 2 includes a pressure generating device 4, a delivery conduit 6, a patient interface device 8, and an elbow connector 10 having an exhaust port 12 provided therein. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through elbow connector 10.

In the illustrated embodiment, patient interface 8 is a nasal/oral mask structured to cover the nose and mouth of the patient. However, other types of patient interface devices, such as, without limitation, a nasal mask that covers the patient's nose or a full face mask that covers the patient's face, which facilitates the delivery of the flow of breathing gas to, and the removal of a flow of exhalation gas from, the airway of a patient may be used while remaining within the scope of the present invention.

Figure 2:
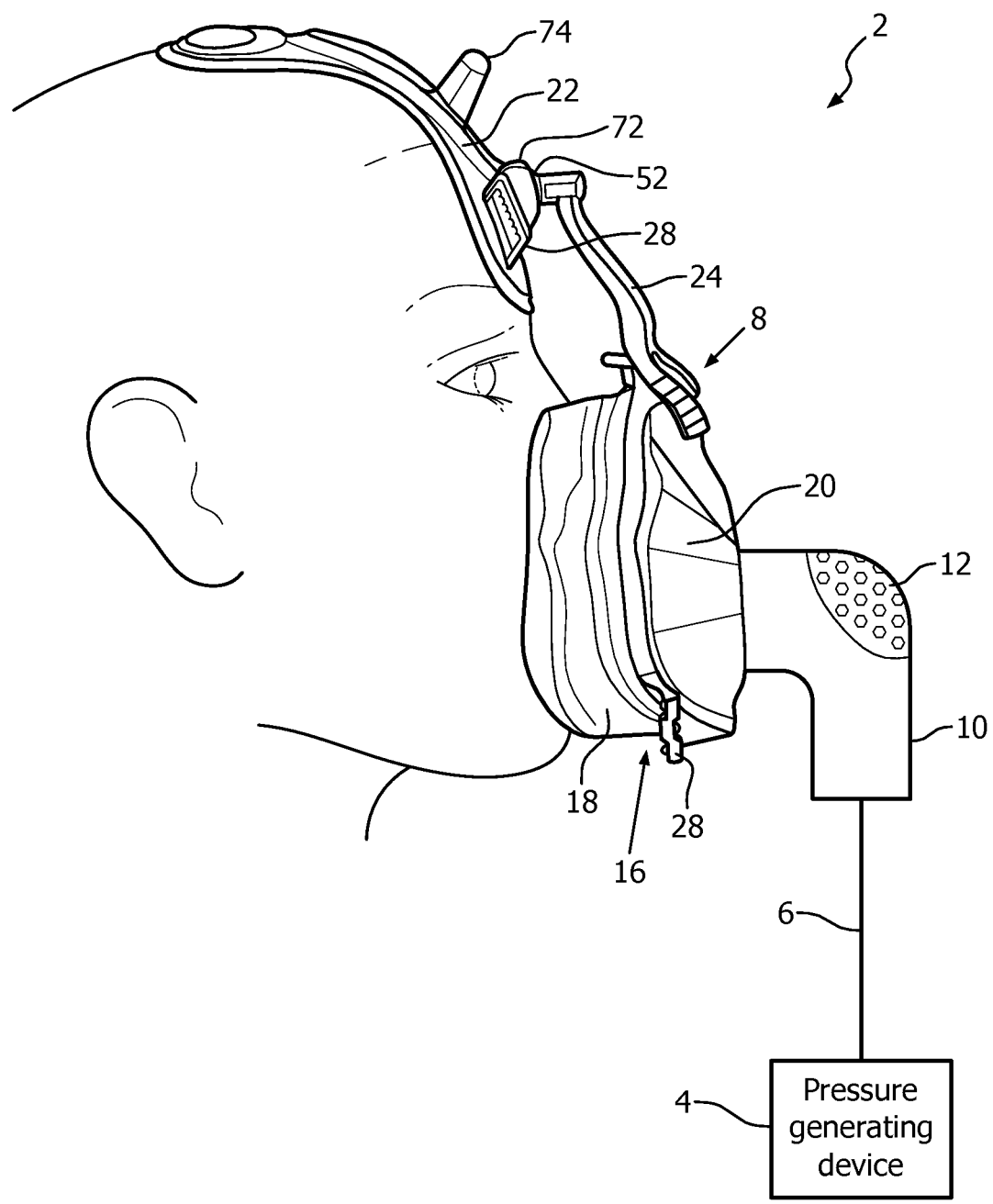

In the embodiment shown in FIGS. 1 and 2, patient interface device 8 comprises a mask component 16 that includes a flexible cushion 18 coupled to a rigid or semi-rigid shell 20. An opening in shell 20 to which elbow connector 10 is coupled allows the flow of breathing gas from pressure generating device 4 to be communicated to an interior space defined by mask component 16, and then, to the airway of a patient. The opening in shell 20 also allows the flow of exhalation gas (from the airway of such a patient) to be communicated to exhaust port 12 of elbow connector 10 in the current embodiment.

Patient interface device 8 further includes a head support member 22 structured to rest on the front portion of the top of the head of the patient, and a coupling arm 24 which couples mask component 16 to head support member 22. Straps (not shown) of a headgear component may be attached to attachment elements 26 provided on either side of shell 20 and to attachment elements 28 provided on either side of head support member 22 to secure patient interface device 8 to the patient's head.

Figure 3:
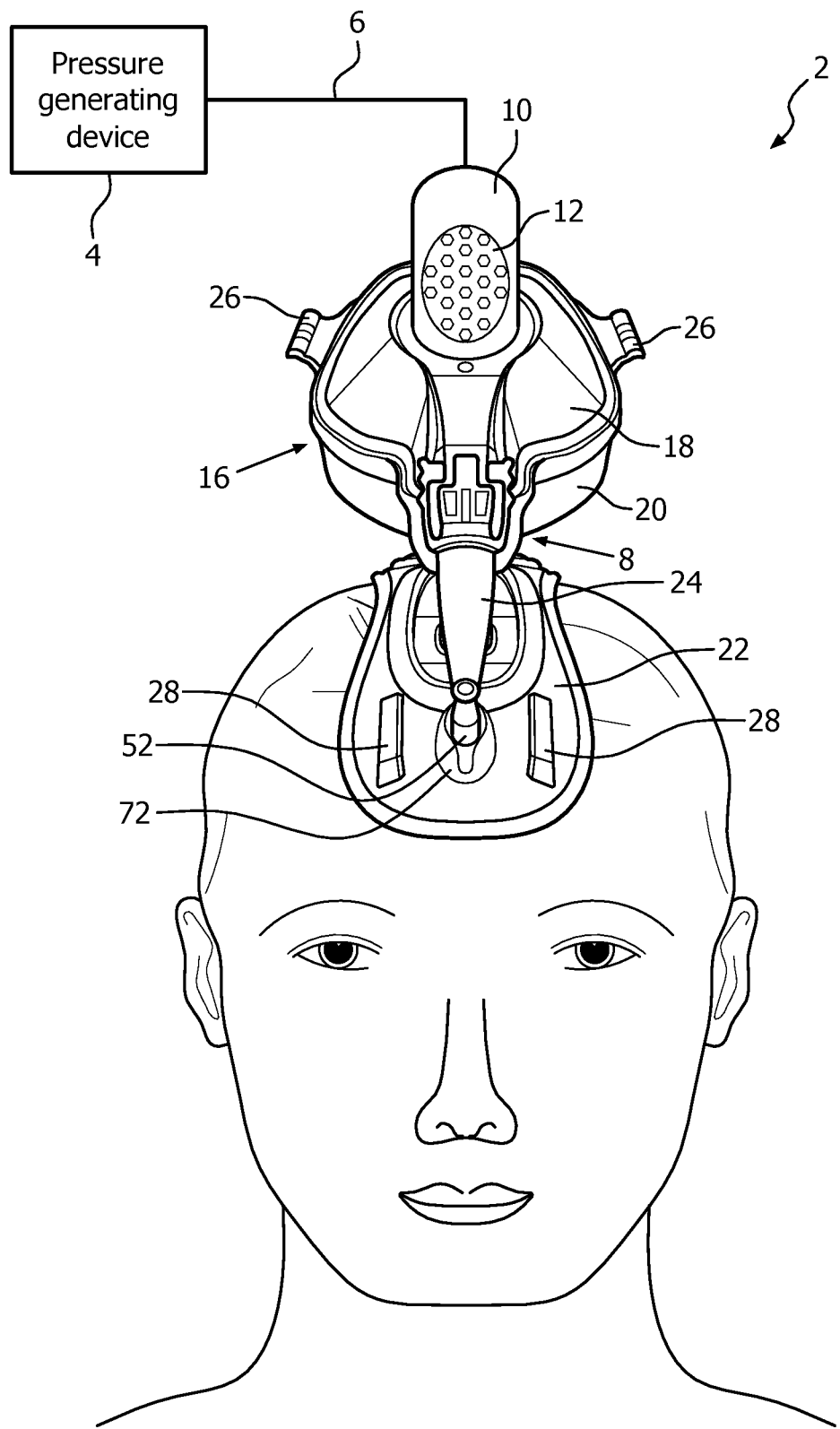
Figure 4:
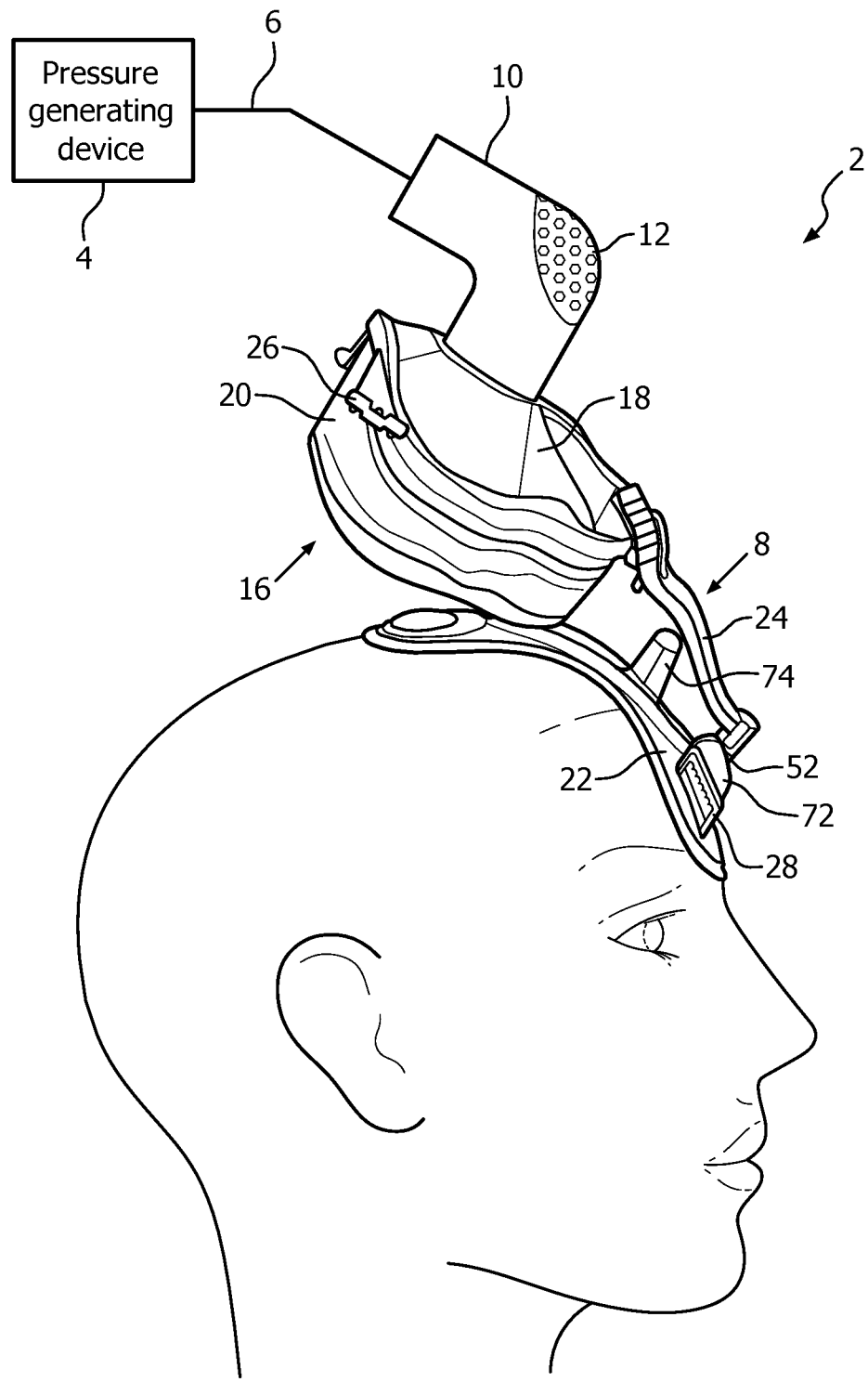

As described in greater detail herein, patient interface device 8 implements a ball-and-socket connection which allows mask component 16 to be selectively moved away from the patient's face in multiple planes to a locked position as shown in FIGS. 3 and 4. In addition, mask component 16 can be rotated 180 degrees in-plane parallel to the patient's face, significantly reducing the hinge-torque problem described elsewhere herein in connection with known configurations. Furthermore, the in-plane rotation affords an improved orientation for locking mask component 16 into position (FIGS. 3 and 4), which in turn does not require the caregiver to manually hold mask component 16 in position during care.

Figure 5:
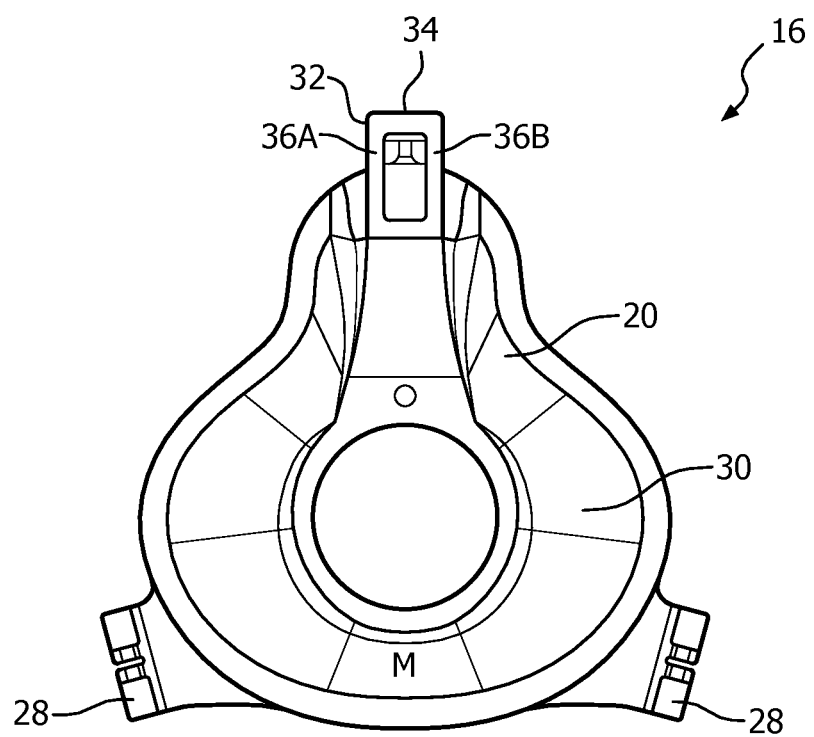
FIG. 5 is a front elevational view and FIG. 6 is a side elevational view of a mask component of the system of FIGS. 1-4.
Figure 6:
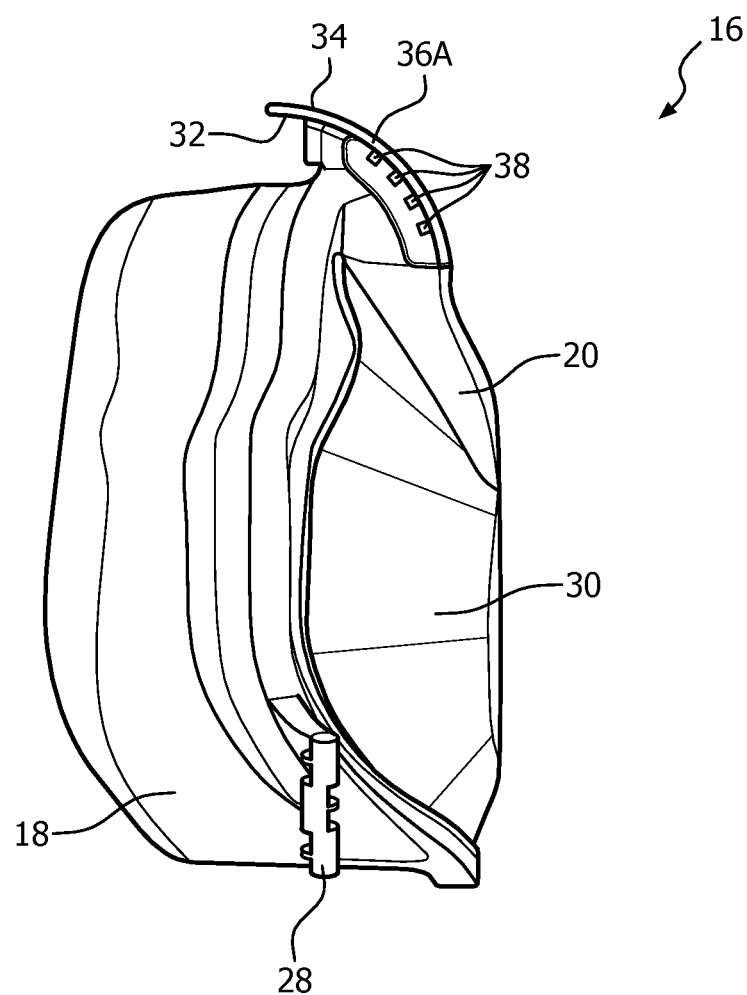
Figure 7:
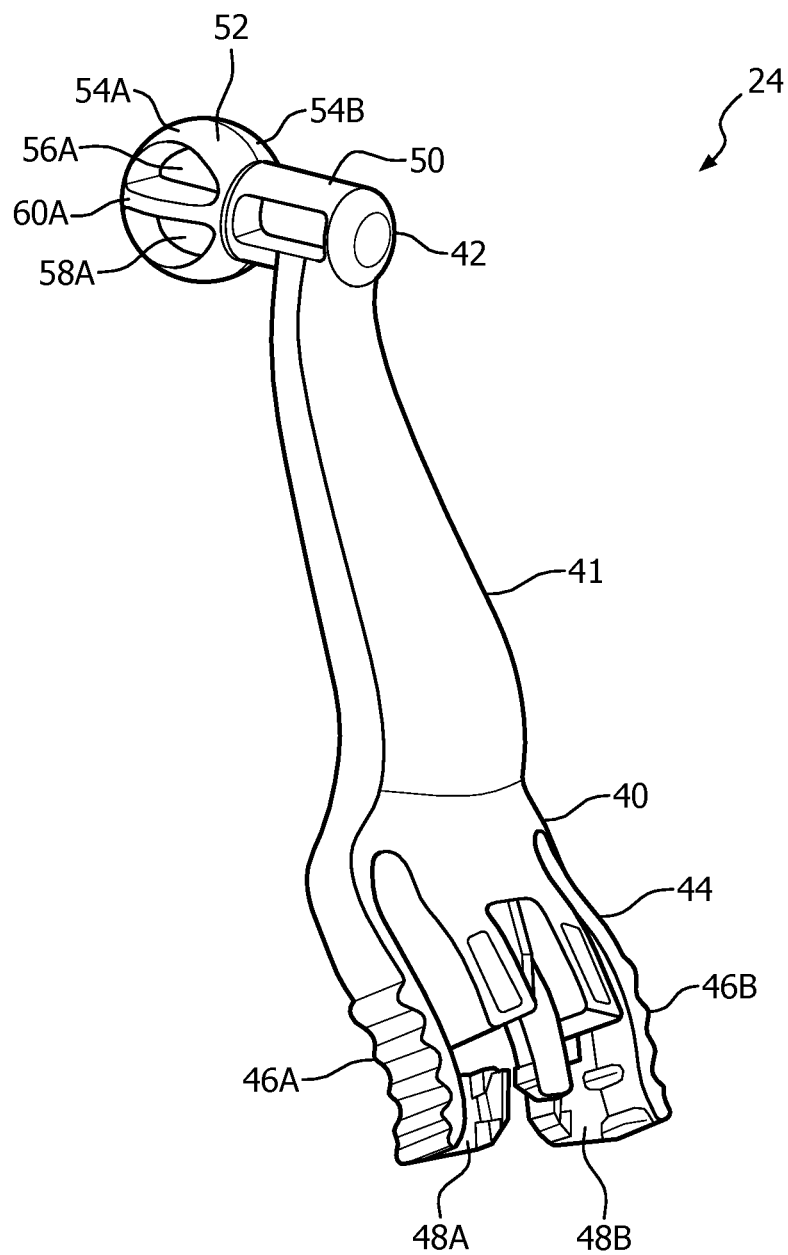
FIGS. 7, 8, 9 and 10 are isometric, front elevational, side elevational and rear elevational views, respectively, of a coupling arm of the system of FIGS. 1-4.
Figure 8:
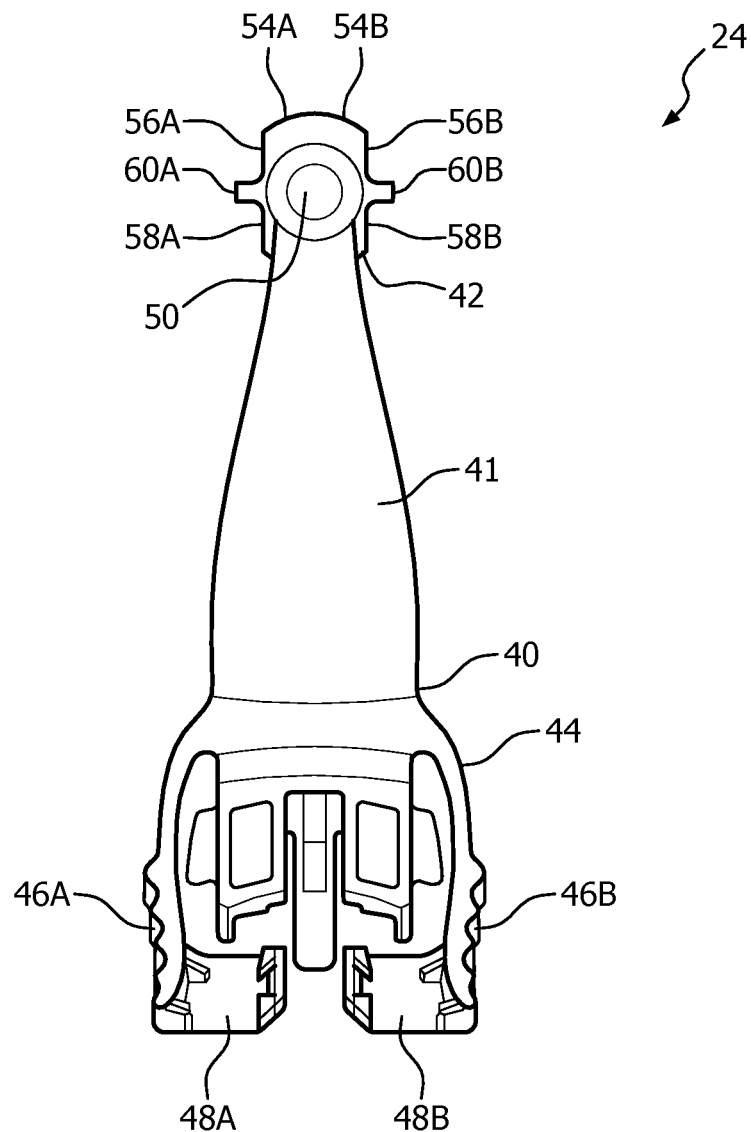
Figure 9:
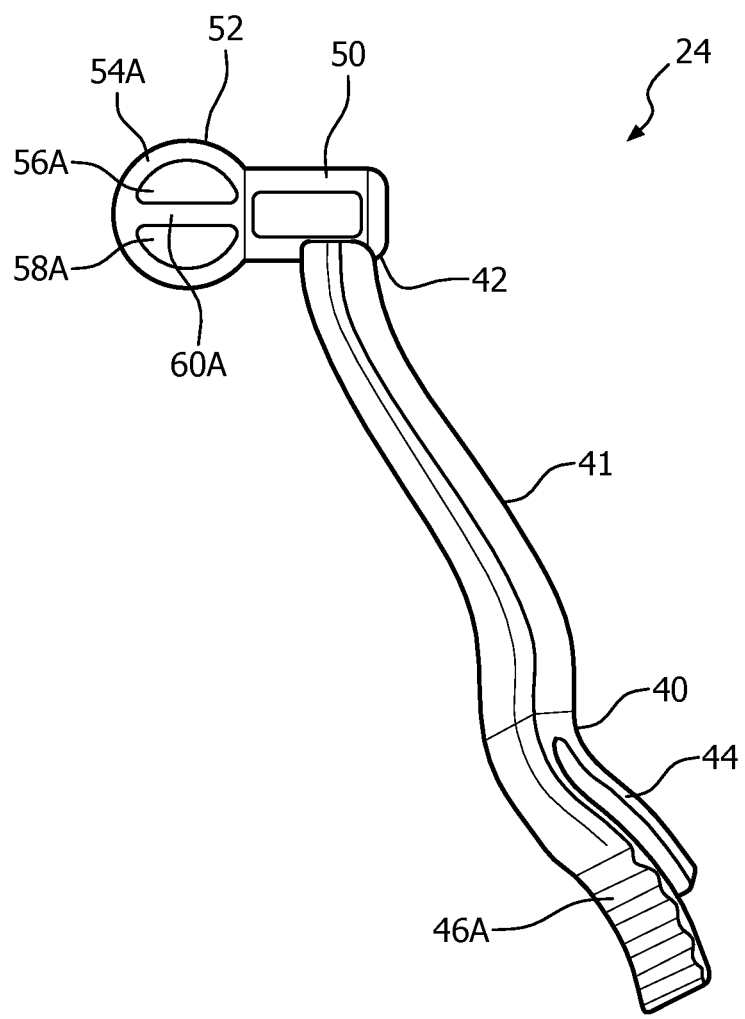

FIG. 5 is a front elevational view and FIG. 6 is a side elevational view of mask component 16 according to the exemplary embodiment. As noted elsewhere herein, mask component includes cushion 18 coupled to shell 20. In the exemplary embodiment, cushion 18 is a unitary structure made of a soft, flexible, cushiony, elastomeric material, such as, without limitation, silicone, an appropriately soft thermoplastic elastomer (such as thermoplastic polyurethanes (TPU)) latex, polybutadiene, a closed cell foam, or any combination of such materials. Also in the exemplary embodiment, shell 20 is made of a material such as, without limitation, a polycarbonate or an injection molded thermoplastic. As described elsewhere herein, shell 20 includes attachment elements 28 on the bottom portion thereof. In addition, as seen in FIGS. 5 and 6, shell 20 further includes a faceplate portion 30 structured to be coupled to elbow connector 10, and an attachment member 32 provided on the top portion thereof. Attachment member 32 is structured to enable shell 20 to be coupled to coupling arm 24. Attachment member 32 includes a track 34 having first and second curved track members 36A, 36B, wherein each track member has a plurality of teeth 38 provided thereon.

FIGS. 7, 8, 9 and 10 are isometric, front elevational, side elevational and rear elevational views, respectively, of coupling arm 24 according to the exemplary embodiment. In the exemplary embodiment, coupling arm 24 is made of a rigid or semi-rigid material such as, without limitation, a polycarbonate or an injection molded thermoplastic, and includes a first end 40 and a second end 42 opposite first end 40, and an elongated central arm portion 41.

First end 40 of coupling arm 24 is structured to enable connection of coupling arm 24 to shell 20. In particular, first end 40 includes an attachment assembly 44 having first and second flexible members 46A, 46B. Attachment assembly 44 is structured to slideably receive track 34 in a manner wherein first end 40 is slideable along attachment member 32 in a curvilinear fashion. In addition, each flexible member 46A, 46B includes a hooked portion 48A, 48B. Flexible members 46A, 46B are structured to flex toward and away from one another to enable the hooked portions 48A, 48B to selectively engage teeth 38 to lock coupling arm 24 in place relative to shell 20 at a desired position.

Second end 42 of coupling arm 24 is structured to enable connection of coupling arm 24 to head support member 22. Second end 42 includes a post 50 that extends in a direction transverse to a longitudinal axis of coupling arm 24. A ball member 52 is provided at the distal end of post 50. Ball member 52 includes first and second halves 54A, 54B. Each half 54A, 54B comprises a first recess 56A, 56B and a second recess 58A, 58B separated by a ridge member 60A, 60B.

Figure 10:
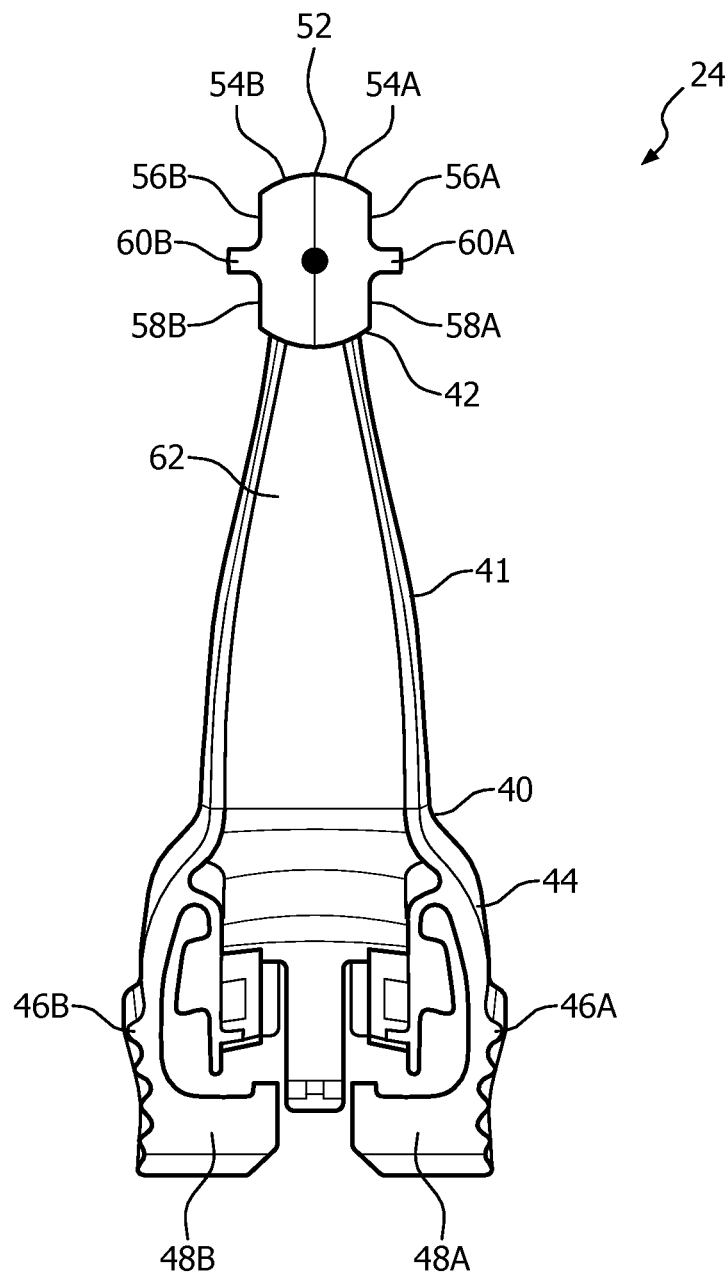

Furthermore, as seen in FIG. 10, the rear of central arm portion 41 includes a channel 62. As described in detail below, channel 62 is structured to provide one part of a locking mechanism for locking coupling arm 24 to head support member 22 when mask component 16 is moved away from the patient's face.

Figure 11:
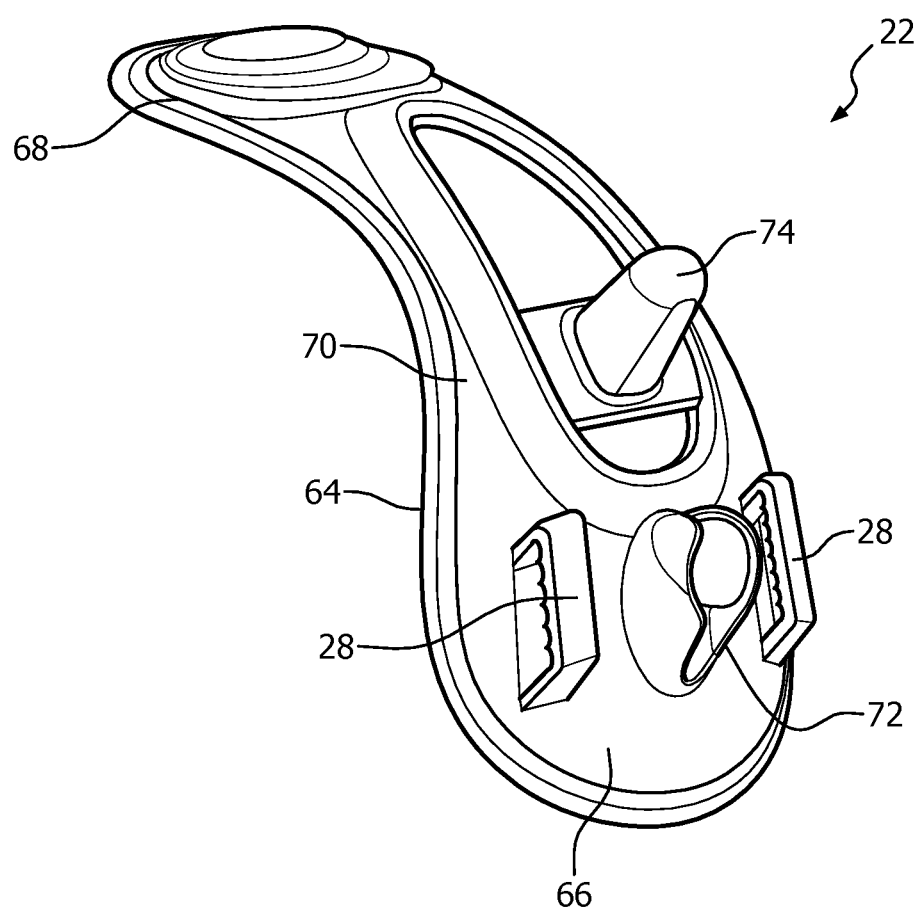
FIGS. 11, 12 and 13 are isometric, front elevational and side elevational views, respectively, of a head support member of the system of FIGS. 1-4.
Figure 12:
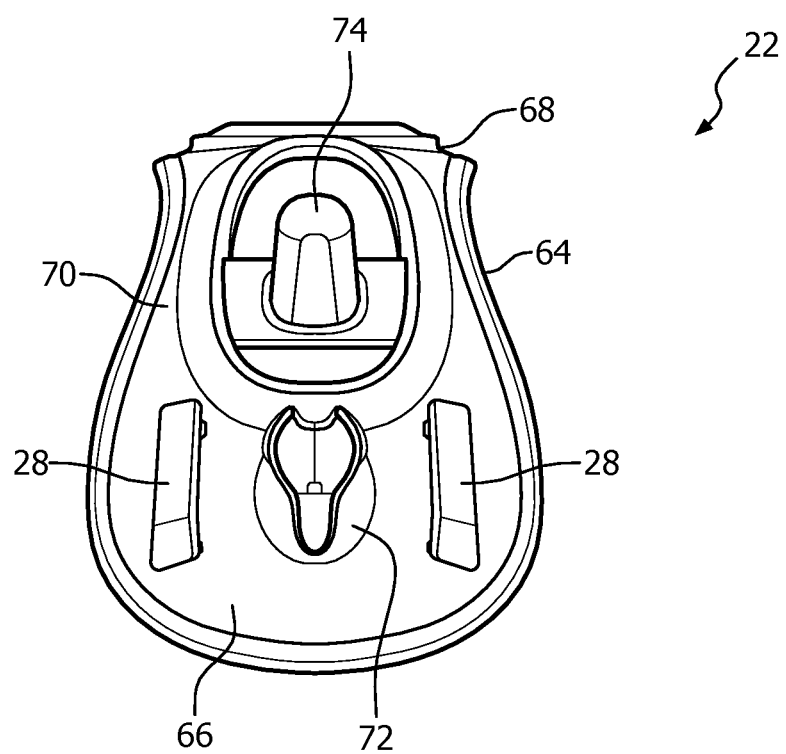
Figure 13:
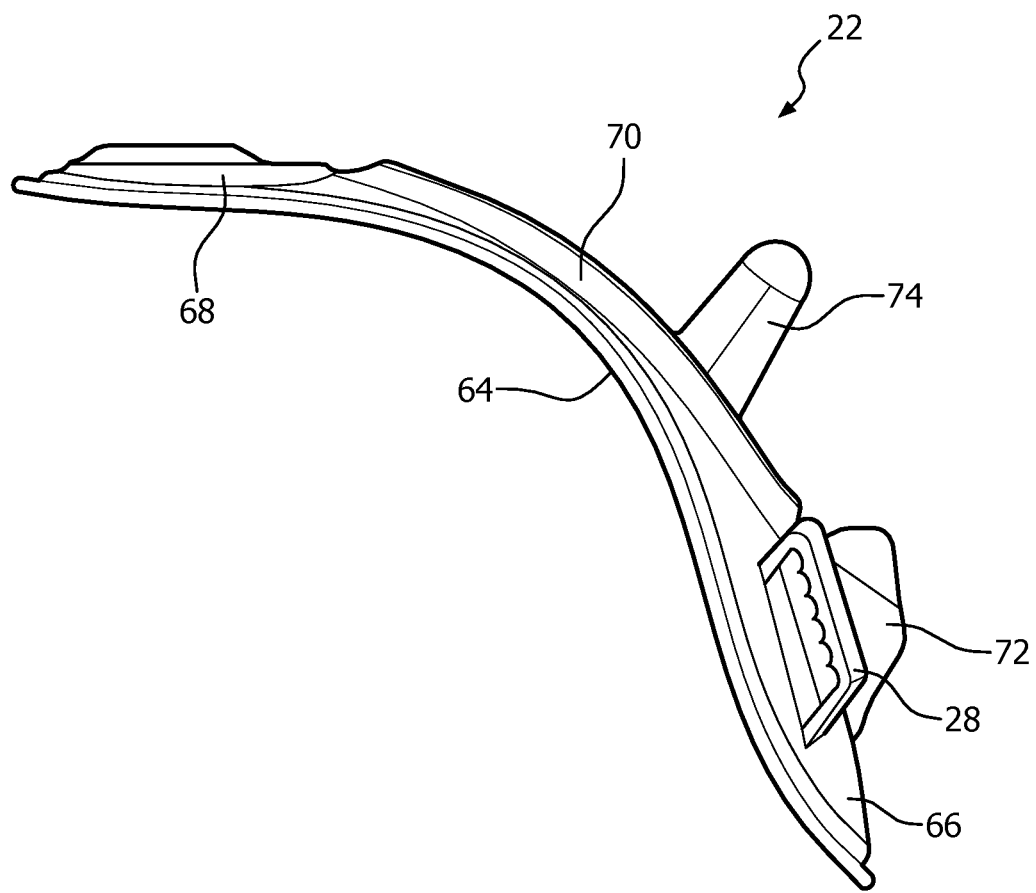

FIGS. 11, 12 and 13 are isometric, front elevational and side elevational views, respectively, of head support member 22 according to the exemplary embodiment. Head support member 22 includes a main body portion 64 that is contoured to generally match the shape of the front portion of the top of the head of the patient. In the exemplary embodiment, head support member 22 is made of a rigid or semi-rigid material such as, without limitation, a polycarbonate or an injection molded thermoplastic, and may, for comfort, include padding on the rear side thereof that is structured to engage the patient's head. Head support member 22 includes a first end 66, a second end 68 opposite first end 66, and a central portion 70.

First end 66 includes a socket member 72 that extends outwardly from a top side of head support member 22. Socket member 72 is structured to receive and hold ball member 52 of coupling arm 24 (FIGS. 1-4) in a manner that allows coupling arm 24 and mask component 16 attached to coupling arm 24 to be selectively moved away from the patient's face in multiple planes. In particular, the operative coupling of ball member 52 to socket member 72 enables mask component 16 to be rotated 180 degrees in a plane parallel to the patient's face, which significantly reduces the hinge-torque problem described elsewhere herein in connection with known configurations.

Furthermore, a post member 74 is provided on central portion 70 in a configuration wherein post member 74 extends outwardly from a top side of head support member 22. Post member 74 is structured to be received and securely held within channel 62 of coupling arm 24 by way of a friction fit when coupling arm 24 and mask component 16 are moved and rotated 180 degrees away from the patient's face as shown in FIGS. 3 and 4. Thus, post member 74 and channel 62 together provide a locking mechanism for holding mask component 16 in position and, as a result, eliminates the need for the caregiver to manually hold mask component 16 in position during care. As seen in FIGS. 3 and 4, when coupling arm 24 and mask component 16 are in the locked position, the front of mask component 16, and thus elbow connector 10 and delivery conduit 6, face and extend away from the patient's head, and thus do not get in the way during the rotation and locking procedure.

Figure 14:
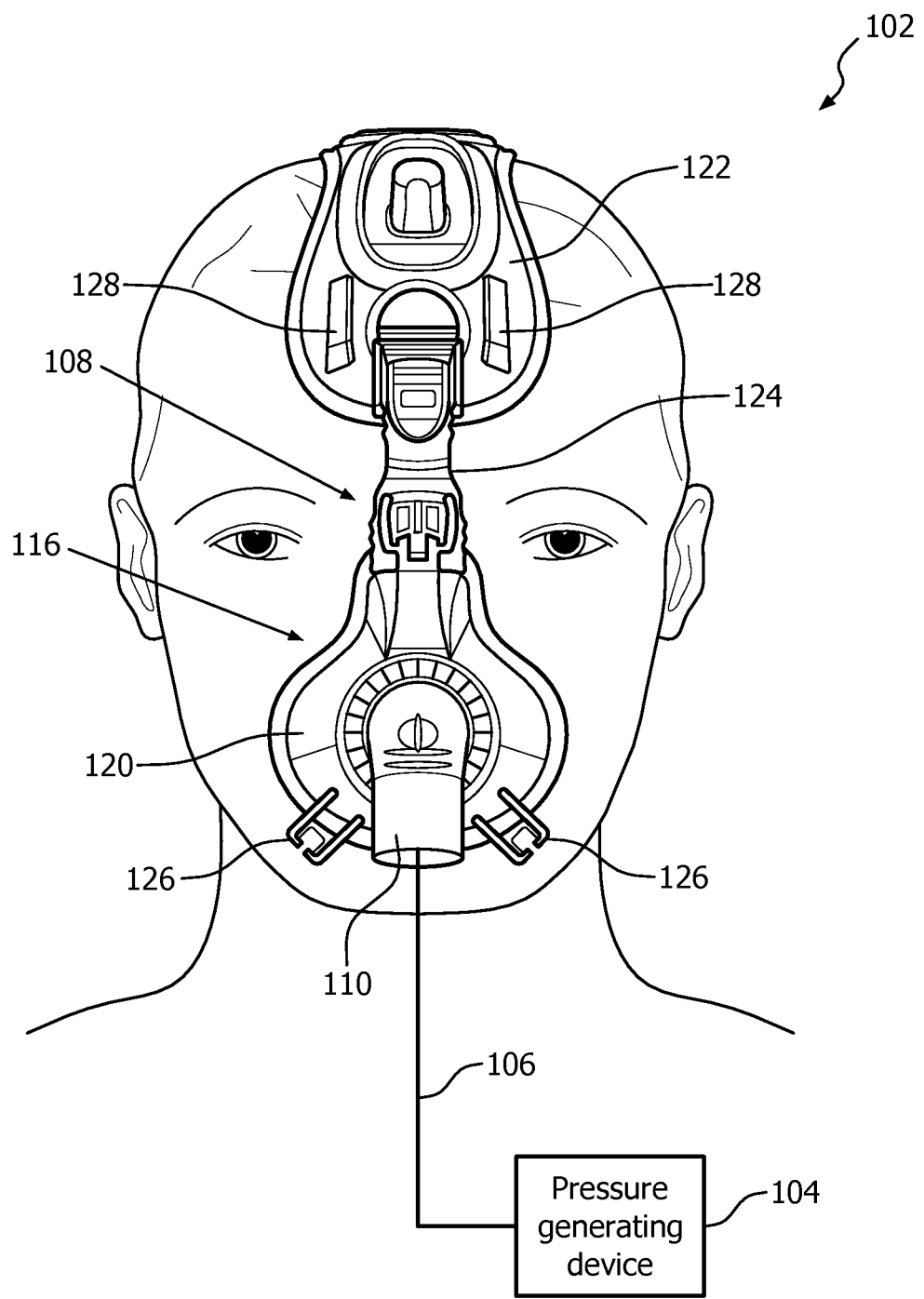
FIGS. 14-17 are schematic diagrams of a system adapted to provide a regimen of respiratory therapy to a patient according to an alternative exemplary embodiment of the invention.
Figure 15:
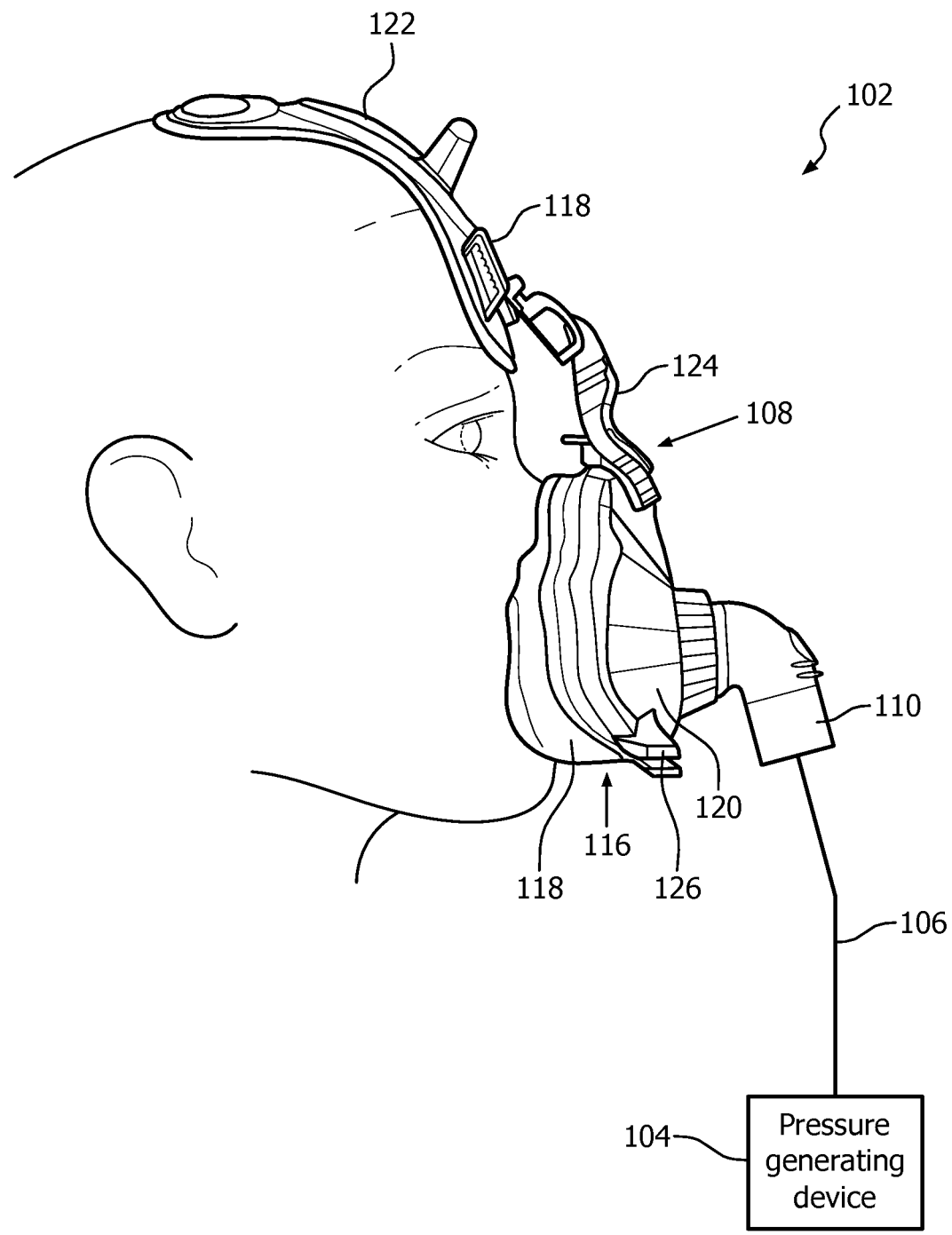

A system 1022 adapted to provide a regimen of respiratory therapy to a patient according to an alternative exemplary embodiment is generally shown in FIGS. 14 (front view) and 15 (side view). System 102 includes a pressure generating device 104, substantially similar to pressure generating device 4 described elsewhere herein, a delivery conduit 106, substantially similar to delivery conduit 6 described elsewhere herein, and an alternative patient interface device 108 described below.

Patient interface device 108 comprises a mask component 116 that is substantially similar to mask component 16 described elsewhere herein, and that includes a flexible cushion 118 coupled to a rigid or semi-rigid shell 120. An opening in shell 120 to which elbow connector 110 is coupled allows the flow of breathing gas from pressure generating device 104 to be communicated to an interior space defined by mask component 116, and then, to the airway of a patient. The opening in shell 120 also allows the flow of exhalation gas (from the airway of such a patient) to be communicated to an exhaust port of elbow connector 110 in the current embodiment.

Patient interface device 108 further includes a head support member 122 structured to rest on the front portion of the top of the head of the patient, and a coupling arm assembly 124 which couples mask component 116 to head support member 122. Straps (not shown) of a headgear component may be attached to attachment elements 126 provided on either side of shell 120 and to attachment elements 128 provided on either side of head support member 122 to secure patient interface device 108 to the patient's head.

Figure 16:
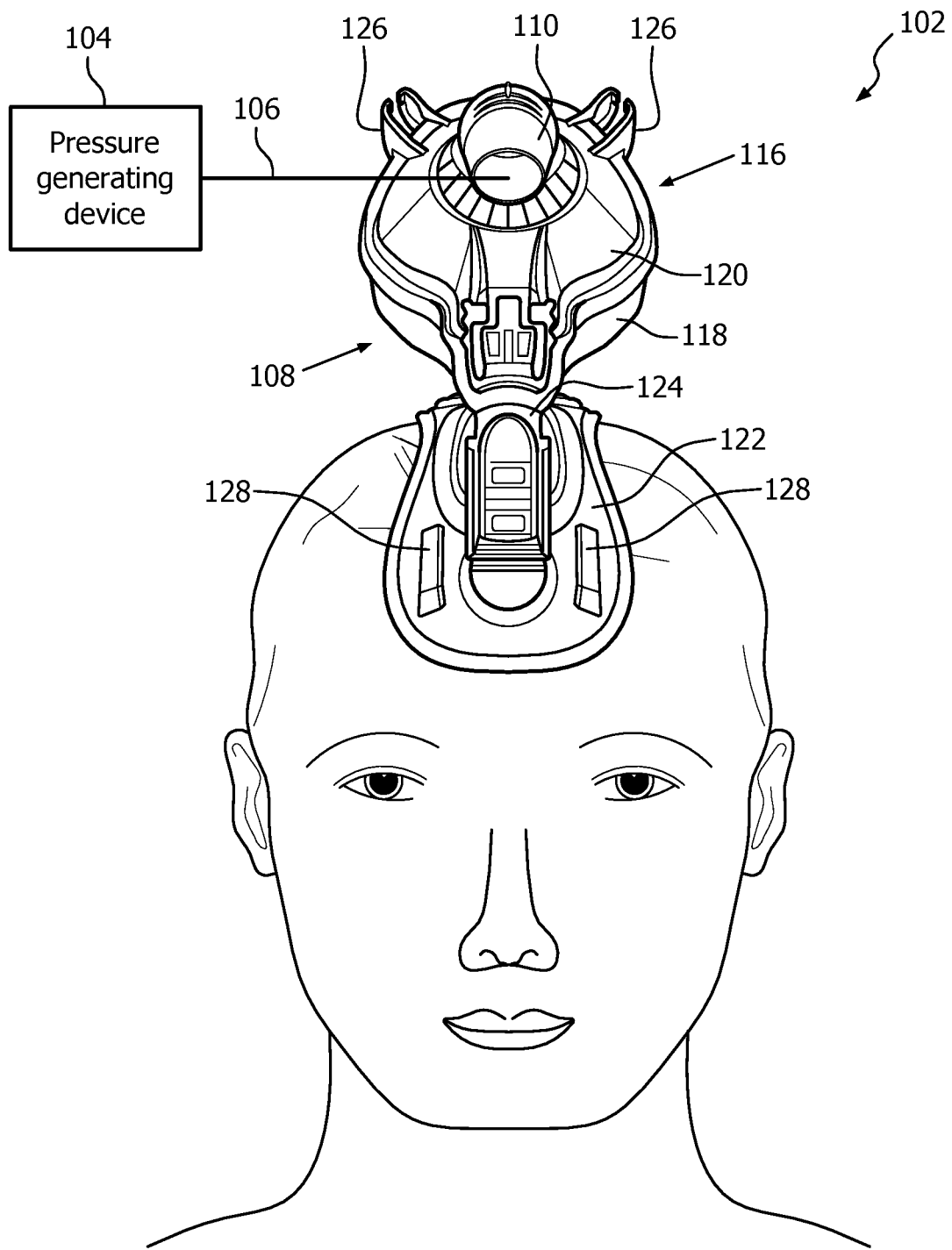
Figure 17:
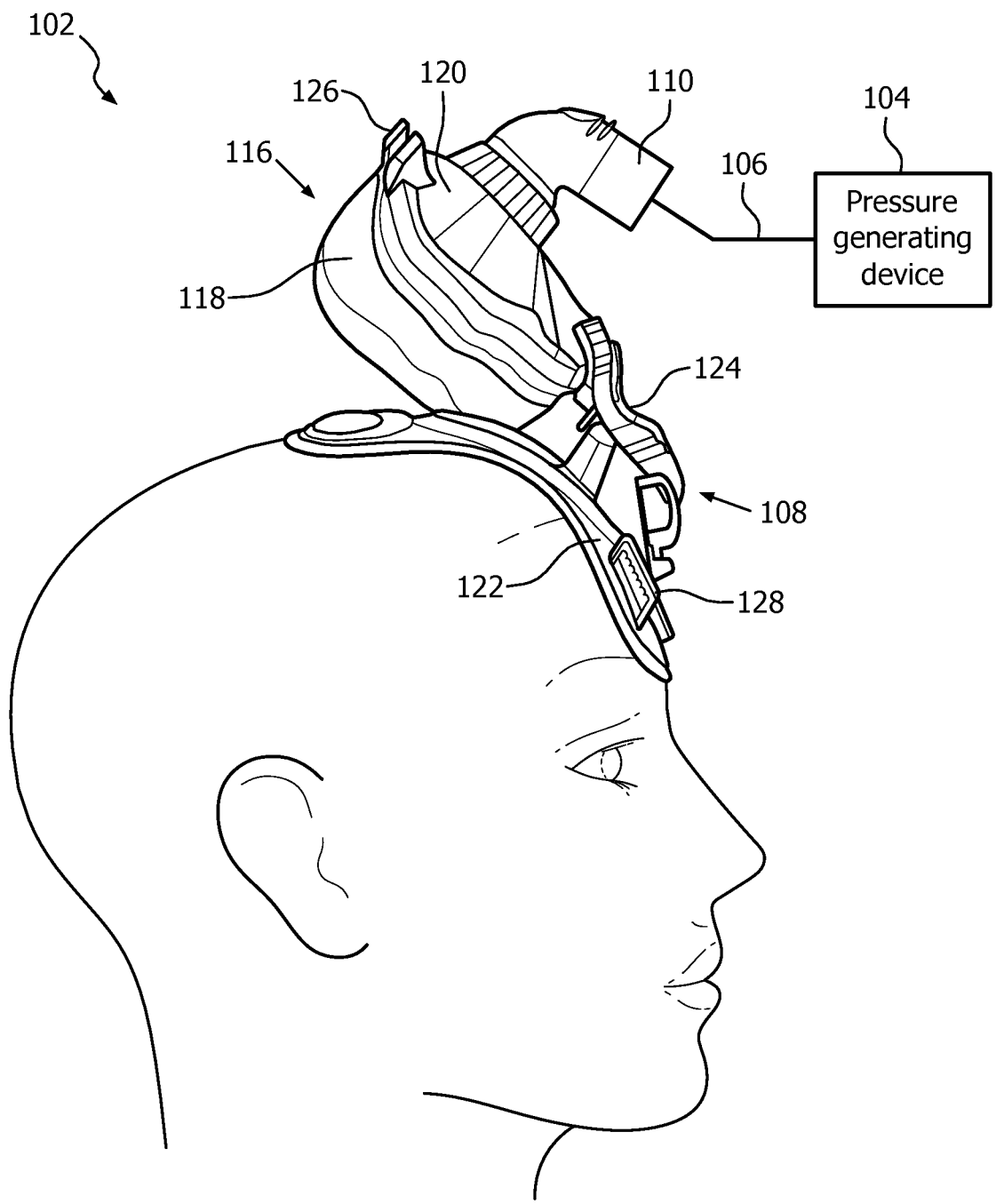
Figure 18:
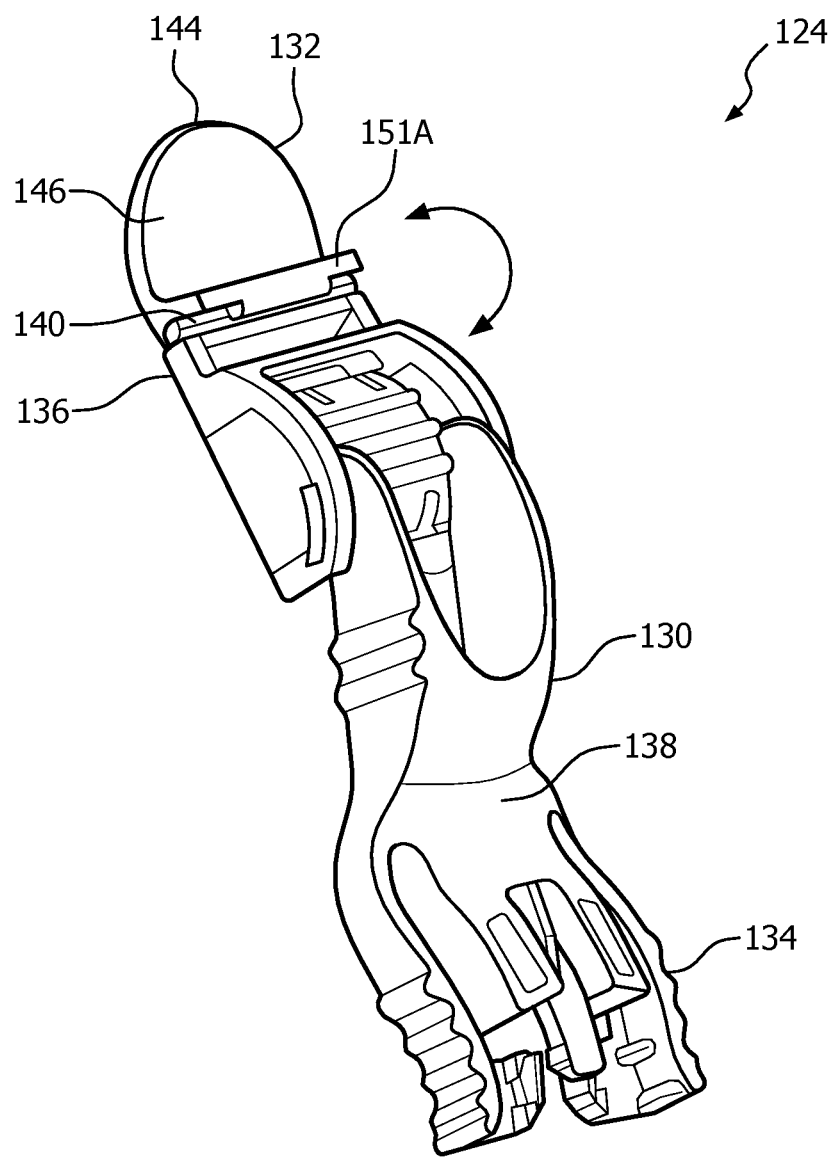
FIGS. 18, 19, 20 and 21 are isometric, front elevational, side elevational and rear elevational views, respectively, of a coupling arm assembly of the system of FIGS. 14-17.
Figure 19:
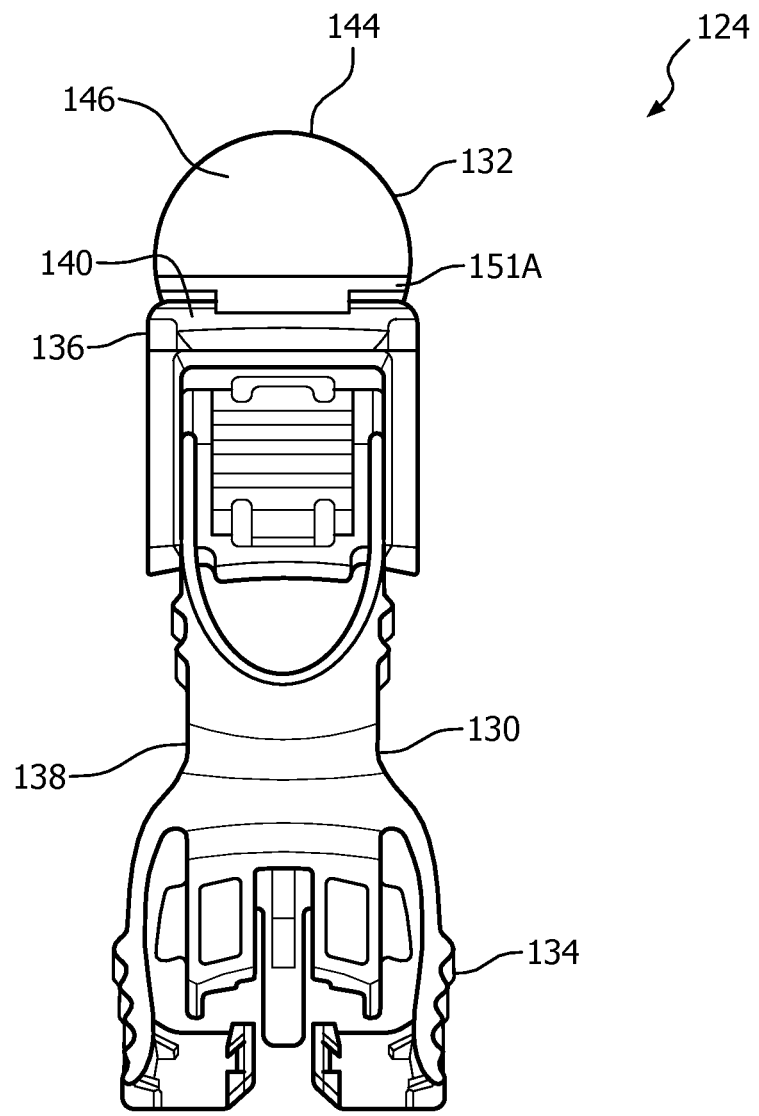
Figure 20:
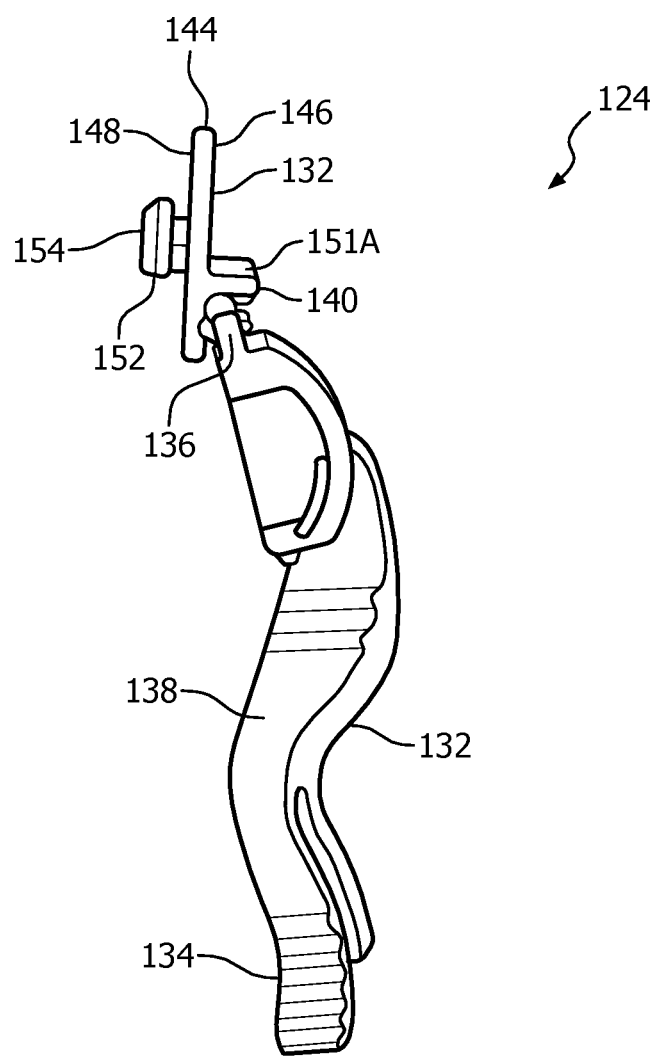

As described in greater detail herein, patient interface device 108 implements a multi-plane hinge connection enabling rotational movement about a first axis and pivoting movement about a second axis perpendicular to the first axis. Thus, the multi-plane hinge connection allows mask component 116 to be selectively moved away from the patient's face in multiple planes to a locked position as shown in FIGS. 16 and 17. In addition, mask component 116 can be rotated 180 degrees in-plane parallel to the patient's face, significantly reducing the hinge-torque problem described elsewhere herein in connection with known configurations. Furthermore, the in-plane rotation affords an improved orientation for locking mask component 116 into position (FIGS. 16 and 17), which in turn does not require the caregiver to manually hold mask component 116 in position during care.

FIGS. 18, 19, 20 and 21 are isometric, front elevational, side elevational and rear elevational views, respectively, of coupling arm assembly 124 according to the exemplary embodiment. In the exemplary embodiment, coupling arm assembly 124 is made of a rigid or semi-rigid material such as, without limitation, a polycarbonate or an injection molded thermoplastic, and includes a pivot arm member 130 coupled to a rotating swivel member 132.

Figure 22:
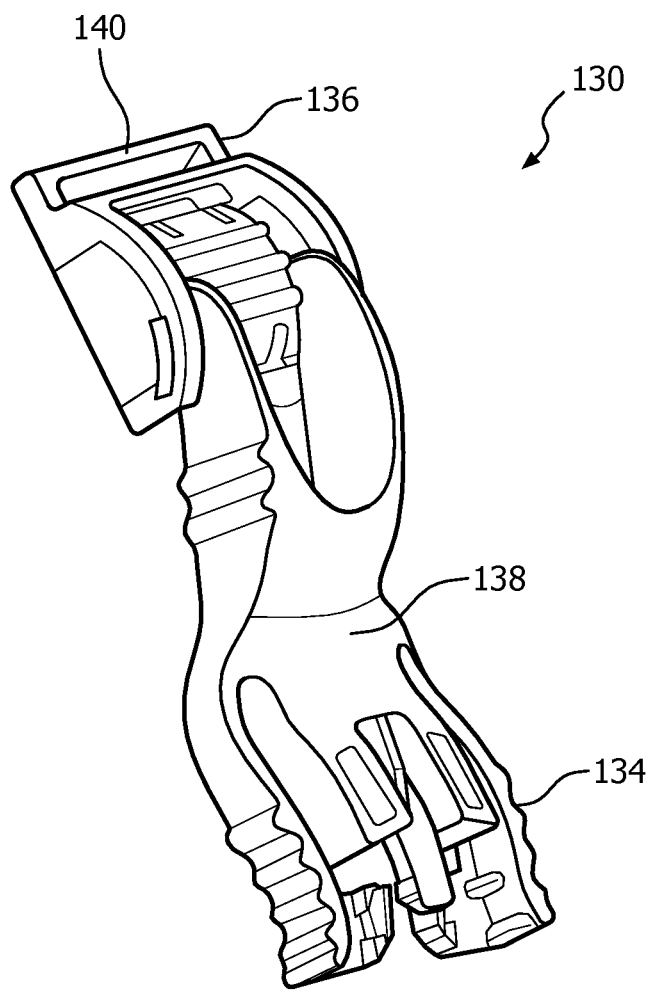
FIGS. 22, 23, and 24 are isometric, front elevational, and side elevational views, respectively, of a pivot arm member forming a part of the coupling arm assembly of FIGS. 18-21.
Figure 23:
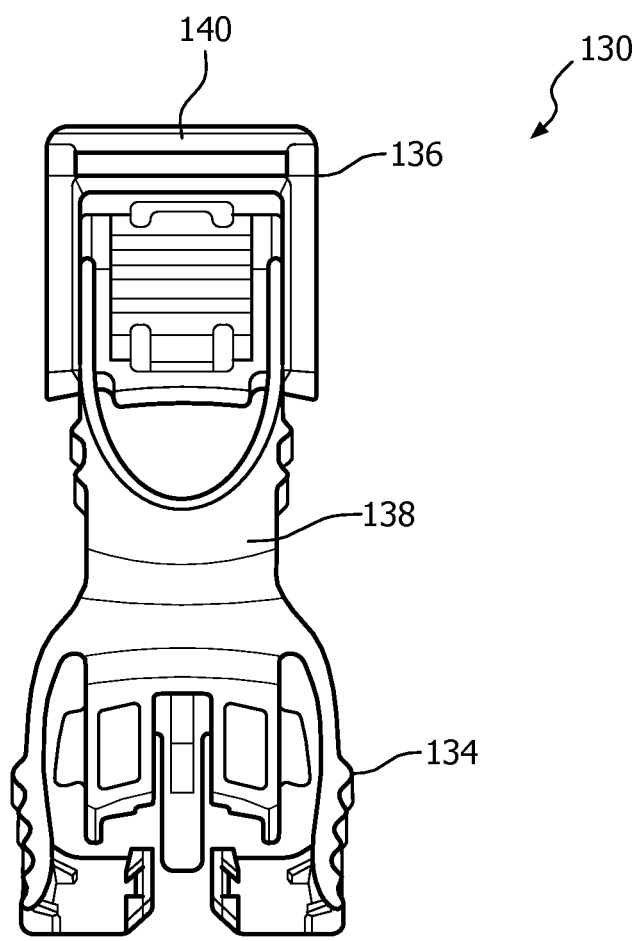
Figure 24:
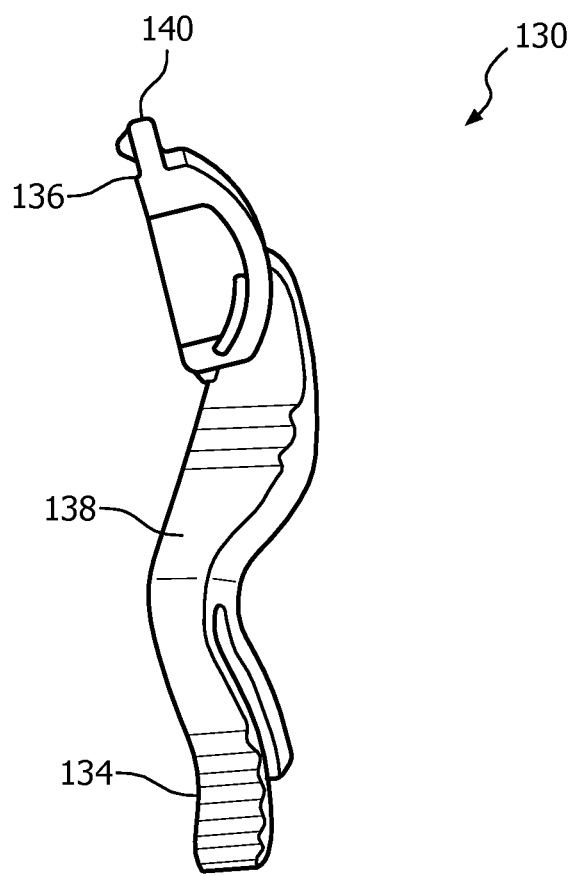

FIGS. 22, 23, and 24 are isometric, front elevational, and side elevational views, respectively, of pivot arm member 130 according to the exemplary embodiment. Pivot arm member 130 includes a first end 134, a second end 136 opposite first end 134, and an elongated central arm portion 138. First end 134 is substantially similar to first end 40 of coupling arm 24 described elsewhere herein and thus is structured to enable connection of assembly 124 to shell 120 in the manner described elsewhere herein. Second end 136 includes a post member 140 that is structured to enable connection of pivot arm member 130 to rotating swivel member 132 in a manner that, as described in greater detail herein, permits pivot arm member 130 to rotate relative to rotating swivel member 132 about the longitudinal axis of post member 140.

Figure 21:
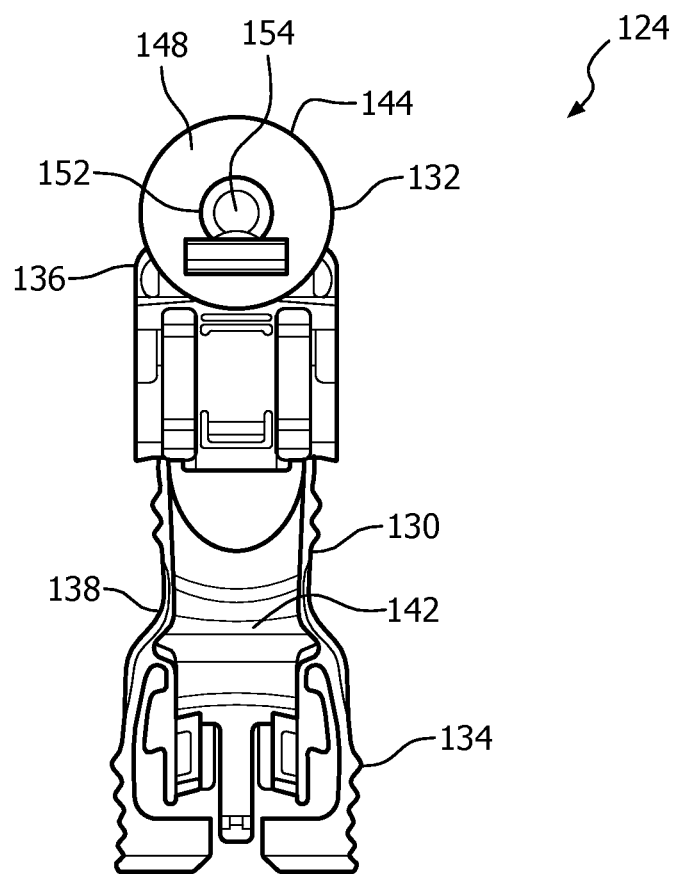

Furthermore, as seen in FIG. 21, the rear of central arm portion 138 includes a channel 142. As described in detail below, channel 142 is structured to provide one part of a locking mechanism for locking coupling arm assembly 124 to head support member 122 when mask component 116 is moved away from the patient's face.

Figure 25:
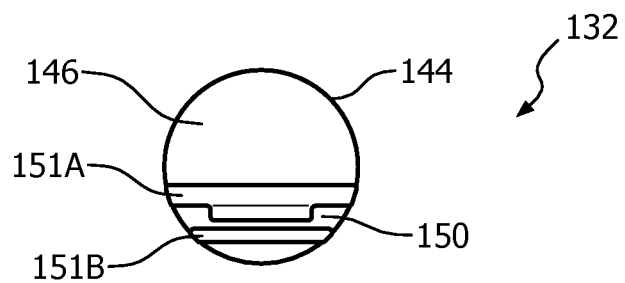
FIGS. 25, 26 and 27 are front elevational, rear elevational, and side elevational views, respectively, of a rotating swivel member forming a part of the coupling arm assembly of FIGS. 18-21.
Figure 26:
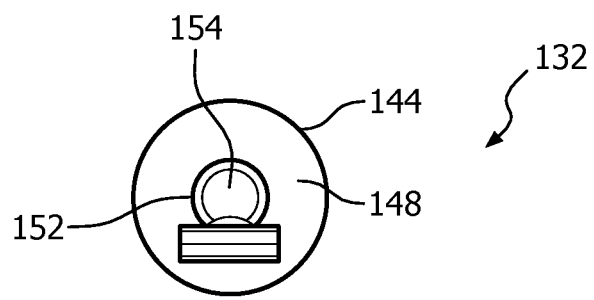
Figure 27:
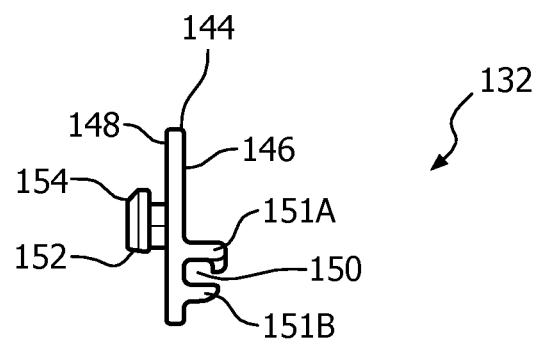

FIGS. 25, 26 and 27 are front elevational, rear elevational, and side elevational views, respectively, of rotating swivel member 132 according to the exemplary embodiment. Rotating swivel member 132 includes a disk shaped circular base member 144 having a front side 146 and a rear side 148. A channel 150 defined by arms 151A, 151B is provided on front side 146. A post member 152 having an enlarged member 154 at the distal end thereof is provided on rear side 148.

Coupling arm assembly 124 is assembly by inserting post member 140 of pivot arm member 130 into channel 150 of rotating swivel member 132. When this is done, pivot arm member 130 is able to rotate relative to rotating swivel member 132 about the longitudinal axis of post member 140 as shown by the arrows in FIG. 18.

Figure 28:
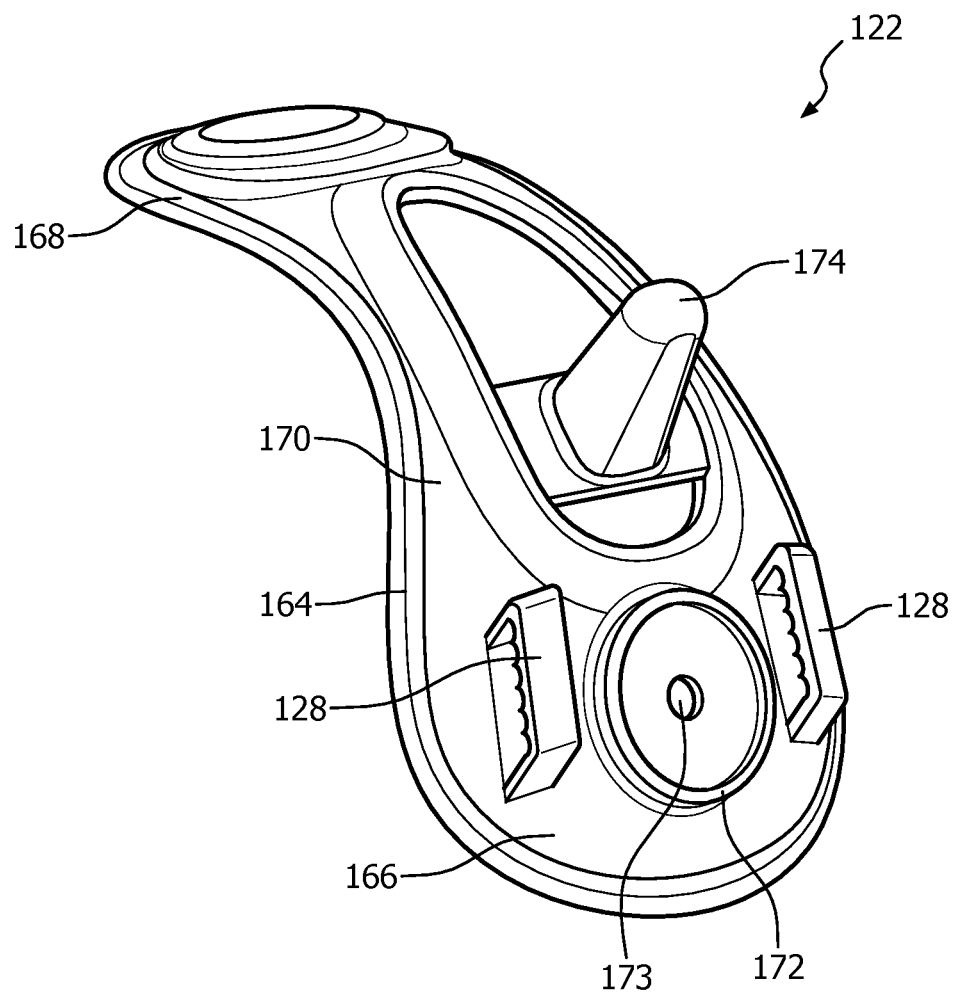
FIGS. 28, 29 and 30 are isometric, front elevational and side elevational views, respectively, of a head support member of the system of FIGS. 14-17.
Figure 29:
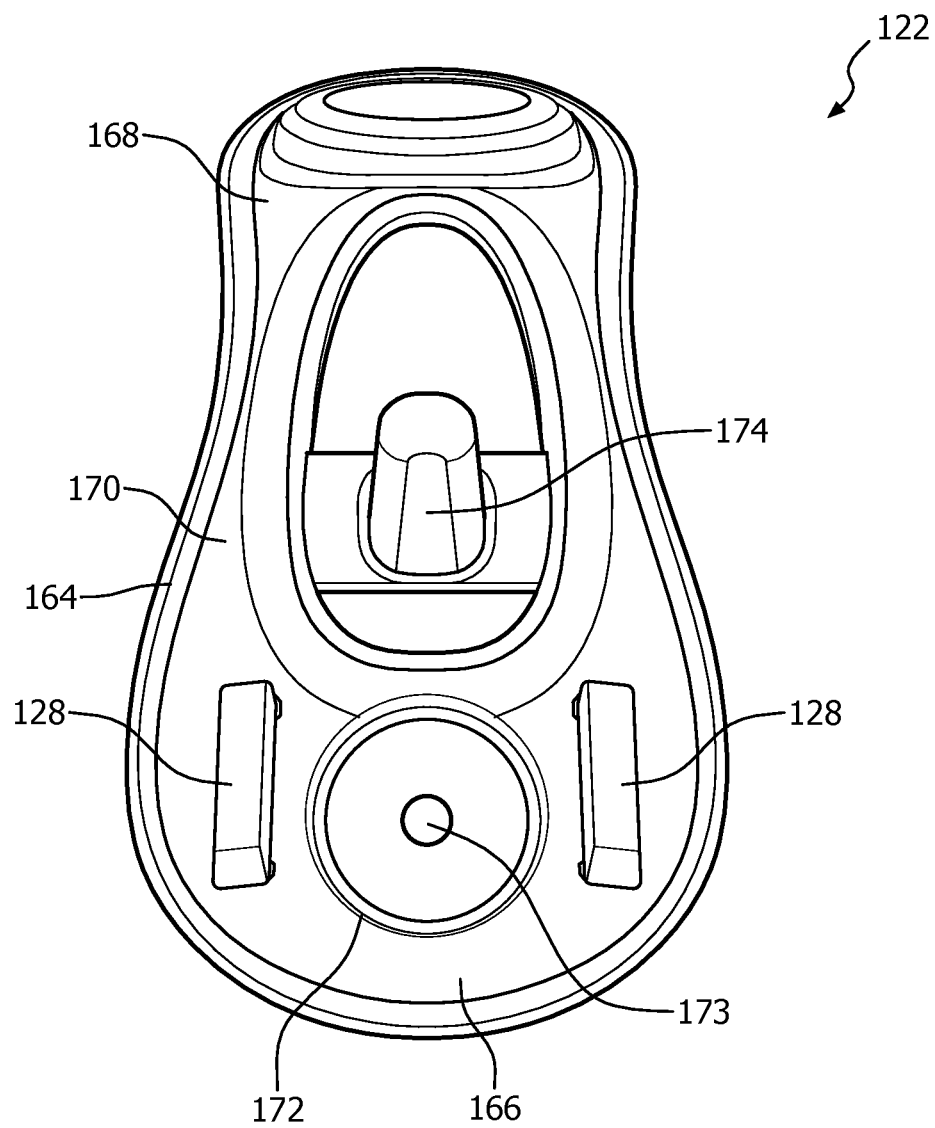
Figure 30:
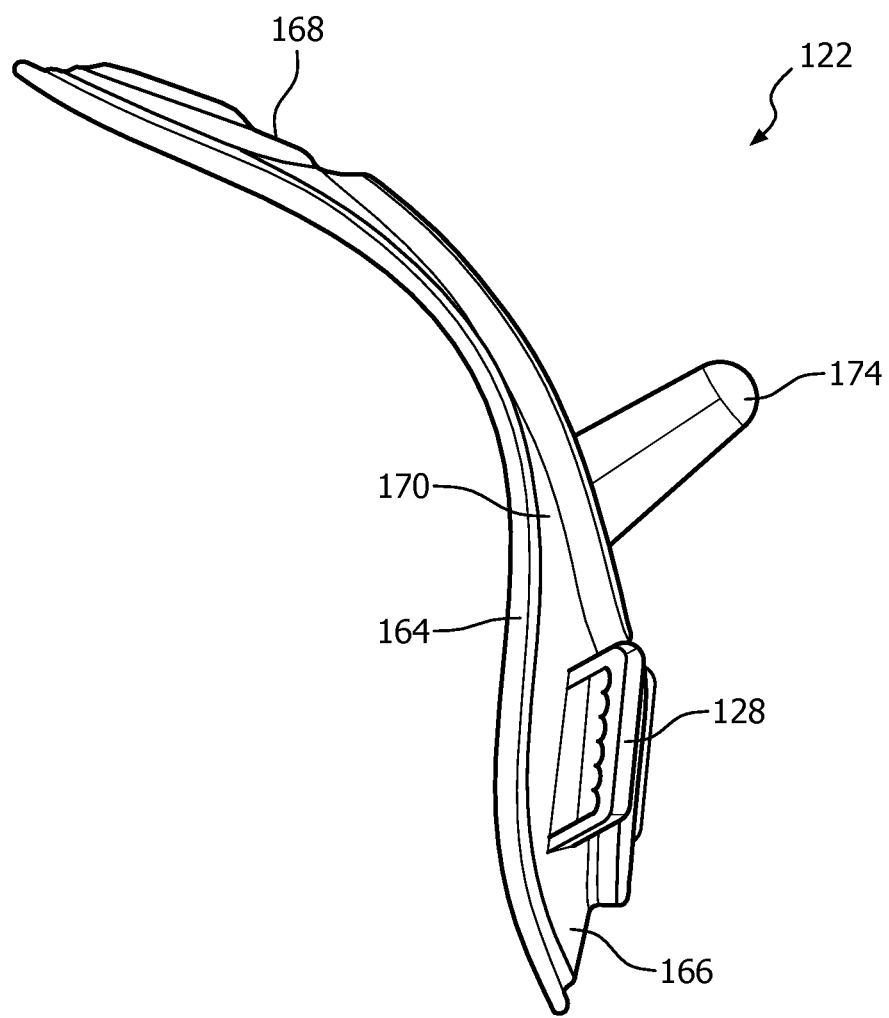

FIGS. 28, 29 and 30 are isometric, front elevational and side elevational views, respectively, of head support member 122 according to the exemplary embodiment. Head support member 122 includes a main body portion 164 that is contoured to generally match the shape of the front portion of the top of the head of the patient. In the exemplary embodiment, head support member 122 is made of a rigid or semi-rigid material such as, without limitation, a polycarbonate or an injection molded thermoplastic, and may, for comfort, include padding on the rear side thereof that is structured to engage the patient's head. Head support member 122 includes a first end 166, a second end 168 opposite first end 166, and a central portion 170.

First end 166 includes a receptacle member 172 that, in the illustrated embodiment, comprises a cylindrical member that extends outwardly from a top side of head support member 122 and defines a recess. Receptacle member 172 includes an orifice 173 in the center thereof. Receptacle member 172 is structured to receive and hold rotating swivel member 132 of coupling arm assembly 124 in a manner that allows rotating swivel member 132 to freely rotate within receptacle member 172. In particular, base member 144 of rotating swivel member 132 is inserted into receptacle member 172 such that post member 152 is received through orifice 173. When this is done, coupling arm assembly 124 is able to rotate relative to head support member 122 within receptacle member 172.

Thus, by way of rotation of pivot arm member 130 relative to rotating swivel member 132 and rotation of rotating swivel member 132 within receptacle member 172, coupling arm assembly 124 and mask component 116 attached to coupling arm assembly 124 are able to be selectively moved away from the patient's face in multiple planes. In particular, the operative coupling of pivot arm member 130 to rotating swivel member 132 and rotating swivel member 132 to receptacle member 172 enables mask component 116 to be rotated 180 degrees in a plane parallel to the patient's face, which significantly reduces the hinge-torque problem described elsewhere herein in connection with known configurations.

Furthermore, a post member 174 is provided on central portion 170 in a configuration wherein post member 174 extends outwardly from a top side of head support member 122. Post member 174 is structured to be received and securely held within channel 142 of coupling arm assembly 124 by way of a friction fit when coupling arm assembly 24 and mask component 116 are moved and rotated 180 degrees away from the patient's face as shown in FIGS. 16 and 17. Thus, post member 174 and channel 142 together provide a locking mechanism for holding mask component 116 in position and, as a result, eliminates the need for the caregiver to manually hold mask component 116 in position during care. As seen in FIGS. 16 and 17, when coupling arm assembly 124 and mask component 116 are in the locked position, the front of mask component 116, and thus elbow connector 110 and delivery conduit 106, face and extend away from the patient's head, and thus do not get in the way during the rotation and locking procedure.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
   a mask component structured to engage a face of the patient;
   a head support member structured to rest on a head of the patient; and
   a coupling arm having a first end coupled to the mask component and a second end coupled to the head support member, wherein the second end of the coupling arm is coupled to the head support member in a manner wherein the mask component is selectively moveable relative to the head support member in multiple planes such that the mask component can be rotated at least 180 degrees in a plane that is parallel to a top surface of the head support member.

2. The patient interface device according to claim 1, wherein the second end of the coupling arm is coupled to the head support member by a ball and socket mechanism.

3. The patient interface device according to claim 2, wherein the ball and socket mechanism comprises a ball member provided at the second end of the coupling arm and a socket member provided at a first end of the head support member.

4. The patient interface device according to claim 1, wherein the second end of the coupling arm is coupled to the head support member by a multi-plane hinge connection enabling rotational movement about a first axis and pivoting movement about a second axis perpendicular to the first axis.

5. The patient interface device according to claim 4, wherein the coupling arm comprises a coupling arm assembly including a pivot arm member coupled to a rotating swivel member wherein the rotating swivel member includes a channel and the pivot arm member includes a post member that defines the second axis, wherein the post member is received within the channel in a manner that allows the pivot arm member to pivot about the second axis, and wherein the rotating swivel member is coupled to a first end of the head support member in a manner wherein the rotating swivel member is able to rotate relative to the head support member about the first axis.

6. The patient interface device according to claim 1, wherein the mask component has front side and a rear side opposite the front side, the rear side of the mask component being structured to engage the face of the patient, wherein the coupling arm has a front side and a rear side opposite the front side of the coupling arm, wherein the front side of the coupling arm and the front side of the mask component face in the same direction, wherein the patient interface device further comprises a locking mechanism having a first portion provided on the rear side of the coupling arm and a second portion provided on the head support member, wherein the first portion of the locking mechanism is structured to be selectively operatively coupled to the second portion of the locking mechanism to securely connect the coupling arm to the head support member.

7. The patient interface device according to claim 6, wherein the second portion of the locking mechanism comprising a post member provided on the head support member.

8. The patient interface device according to claim 7, wherein the first portion of the locking mechanism comprises a channel provided in the rear side of the coupling arm and structured to receive and hold the post member.

9. The patient interface device according to claim 8, wherein the channel is structured to receive and hold the post member by a friction fit.

10. The patient interface device according to claim 1, wherein the mask component comprises a nasal/oral mask structured to cover a nose and mouth of the patient.

11. The patient interface device according to claim 1, wherein the mask component comprises a cushion member coupled to a shell.

12. A method of adjusting a patient interface device comprising a mask component, a head support member having a bottom surface structured to rest on a head of the patient and a top surface opposite the bottom surface, and a coupling arm having a first end coupled to the mask component and a second end coupled to the head support member, the method comprising:
moving the mask component from a first condition wherein the mask component is located in a first position and engages a face of the patient to a second condition wherein the mask component is located in a second position that is 180 degrees from the first position relative to a plane that is parallel to the top surface of the head support member, wherein the mask component has front side and a rear side opposite the front side, the rear side of the mask component being structured to engage the face of the patient, and wherein in the second condition the rear side of the mask component faces toward the top side of the head support member and the front side of the mask component faces away from the top side of the head support member.

13. The method according to claim 12, wherein the second end of the coupling arm is coupled to the head support member by a ball and socket mechanism in a manner wherein the mask component is selectively moveable relative to the head support member in multiple planes.

14. The method according to claim 12, wherein the second end of the coupling arm is coupled to the head support member by a multi-plane hinge connection enabling rotational movement about a first axis and pivoting movement about a second axis perpendicular to the first axis such that the mask component is selectively moveable relative to the head support member in multiple planes.

15. The method according to claim 12, further comprising securely attaching the coupling arm to the head support member in the second condition.

16. The method according to claim 15, wherein the securely attaching the coupling arm to the head support member in the second condition comprises inserting a post member provided on the head support member into a channel provided on the coupling arm.

* * * * *